(12) United States Patent
Old

(10) Patent No.: US 8,633,220 B2
(45) Date of Patent: Jan. 21, 2014

(54) THERAPEUTIC AGENTS FOR OCULAR HYPERTENSION

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 107 days.

(21) Appl. No.: 13/169,386

(22) Filed: Jun. 27, 2011

(65) Prior Publication Data

US 2012/0015978 A1 Jan. 19, 2012

Related U.S. Application Data

(60) Provisional application No. 61/361,023, filed on Jul. 2, 2010.

(51) Int. Cl.
  *A61K 31/04* (2006.01)
  *C07D 215/38* (2006.01)

(52) U.S. Cl.
  USPC .............................. 514/312; 546/159; 549/69

(58) Field of Classification Search
  USPC .............................. 546/159; 514/312; 549/69
  See application file for complete search history.

(56) References Cited

U.S. PATENT DOCUMENTS

| | | | |
|---|---|---|---|
| 4,166,452 A | 9/1979 | Generales, Jr. | |
| 4,207,341 A | 6/1980 | Hubner | |
| 4,221,815 A | 9/1980 | Weyer | |
| 4,238,506 A | 12/1980 | Stach | |
| 4,256,108 A | 3/1981 | Theeuwes | |
| 4,265,874 A | 5/1981 | Bonsen et al. | |
| 5,643,957 A | 7/1997 | Leone-Bay | |
| 7,427,685 B2 | 9/2008 | Donde et al. | |
| 7,491,748 B2 * | 2/2009 | Tani et al. ..................... | 514/563 |

FOREIGN PATENT DOCUMENTS

| | | |
|---|---|---|
| DE | 2604560 | 8/1977 |
| GB | 1449586 | 9/1976 |
| JP | 2003-073357 | 3/2003 |
| WO | 00-61631 | 10/2000 |
| WO | 2004-022525 | 3/2004 |

OTHER PUBLICATIONS

Reminton's Pharmaceutical Sciences, Mack Publishing Company, Easton, Pa., 16th Edition, 1980.
Alois Fürstner, 2002, Iron-Catalyzed Cross-Coupling Reactions of Alkyl-Grignard Reagents with Aryl Chlorides, Tosylates, and Triflates**, Angew. Chem. Int. Ed., 41, 609-612, WILEY-VCH, Weinheim, Germany.
Remington's Pharmaceutical Sciences, 16th Edition, 1980.
Shinichi Uesato, 2002, Novel Histone Deacetylase Inhibitors: N-Hydroxycarboxamides Possessing a Terminal Bicyclic Aryl Group, Bioorganic & Medicinal Chemistry Letters, 12, 1347-1349.
Taishi Maeda, 2004, Potent Histone Deacetylase Inhibitors: N-Hydroxybenzamides With Antitumor Activities, Bioorganic & Medicinal Chemistry, 12, 4351-4360.

* cited by examiner

*Primary Examiner* — D M Seaman

(74) *Attorney, Agent, or Firm* — Krishna Banerjee; Debra D. Condino

(57) ABSTRACT

This invention provides well defined 6-alkyl or hydroxyalkyl-1-naphthamide or quinoline compounds for treating glaucoma or ocular hypertension.

11 Claims, No Drawings

THERAPEUTIC AGENTS FOR OCULAR HYPERTENSION

RELATED APPLICATION

This application claims the benefit of U.S. Provisional Application Ser. No. 61/361,023 filed Jul. 2, 2010, the disclosure of which is hereby incorporated in its entirety herein by reference.

FIELD OF THE INVENTION

This invention relates generally to compounds and methods for the treatment of ocular disorders, and more particularly to the use of well defined 6-alkyl or hydroxyalkyl-1-naphthamide or quinoline compounds for the treatment of glaucoma and ocular hypertension.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

SUMMARY OF THE INVENTION

This invention provides well defined 6-alkyl or hydroxyalkyl-1-naphthamide or quinoline compounds for treating glaucoma or ocular hypertension. In one embodiment of the invention, there are provided compounds having the structure

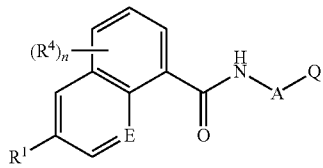

wherein:
E is C or N;
A is —$(CH_2)_m$—Ar—$(CH_2)_o$— wherein Ar is interarylene or heterointerarylene, the sum of m and o is from 1 to 4, and wherein one $CH_2$ may be substituted with S or O;
Q is —$CO_2R^2$, —$CH_2OR^2$, —$CONR^2R^3$, —$COR^3$, —$SO_2R^3$ or tetrazol-5-yl;
$R^1$ is H, alkoxy, or $C_1$-$C_{20}$ linear alkyl, branched alkyl, or cycloalkyl, optionally substituted with one or more —OH moieties;
$R^2$ is hydrogen, $C_1$-$C_6$ alkyl, hydroxyethyl, $CH_3$, phenyl, or biphenyl; and
$R^3$ is hydrogen, $C_1$-$C_6$ linear or branched alkyl, —$COR^2$ or —$SO_2R^2$;
each $R^4$ is independently selected from F, Cl, I, or Br; and
n is 0 to 6;
or a pharmaceutically acceptable salt thereof.

In another embodiment of the invention, there are provided compositions including at least one compound of the invention, wherein the composition is a liquid which is ophthalmically acceptable.

In another embodiment of the invention there are provided methods for treating glaucoma or ocular hypertension. Such methods can be performed, for example, by administering to a subject in need thereof a compound of the invention.

In still another embodiment of the invention, there are provided kits including at least one composition of the invention, a container, and instructions for administration of the composition to a subject in need thereof for the treatment of glaucoma or ocular hypertension.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —$CH_2O R_7$, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further hearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

As used herein "interarylene" refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

As used herein tetrazol-5-yl refers to a moiety having the tautomeric forms depicted below:

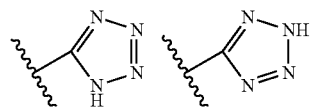

The two tautomeric forms rapidly interconvert in aqueous or biological media and are thus equivalent to one another.

It will be readily apparent to those skilled in the art that some of the compounds of the invention may contain one or more asymmetric centers, such that the compounds may exist in enantiomeric as well as in diastereomeric fauns. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

The invention provides well-defined compounds having the structure:

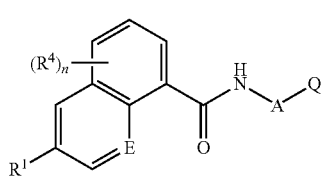

I wherein:
E is C or N;
A is —$(CH_2)_m$—Ar—$(CH_2)_o$— wherein Ar is interarylene or heterointerarylene, the sum of m and o is from 1 to 4, and wherein one $CH_2$ may be substituted with S or O;

Q is —CO$_2$R$^2$, —CONR$^2$R$^3$, —COR$^3$, SO$_2$R$^3$ or tetrazol-5-yl;

R$^1$ is H, alkoxy, or C$_1$-C$_{20}$ linear alkyl, branched alkyl, or cycloalkyl, optionally substituted with one or more —OH moieties;

R$^2$ is hydrogen, C$_1$-C$_6$ alkyl, hydroxyethyl, CF$_3$, phenyl, or biphenyl; and R$^3$ is hydrogen, C$_1$-C$_6$ linear or branched alkyl, —COR$^2$ or —SO$_2$R$^2$;

each R$^4$ is independently selected from F, Cl, I, or Br; and n is 0 to 6;

or a pharmaceutically acceptable salt thereof.

In some embodiments of the invention, there are provided invention compounds wherein R$^1$ is C$_1$-C$_{10}$alkyl. In other embodiments, R$^1$ is C$_6$ alkyl.

In some embodiments of the invention, Ar is phenylene or thiophenylene.

In other embodiments R$^2$ is hydroxyethyl or isopropyl. In still further embodiments, R$^4$ is F.

Exemplary compounds contemplated for use in the practice of the invention include, but are not limited to, compounds having any one of the following structures:

Compound 1

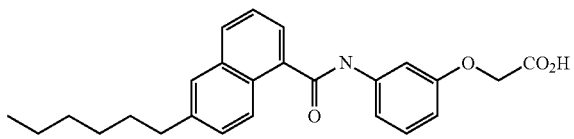

Compound 2

Compound 3

Compound 4

Compound 5

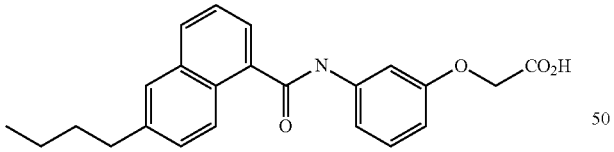

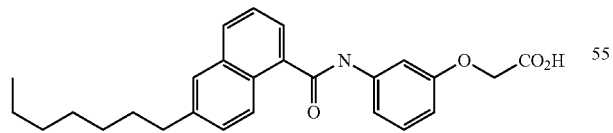

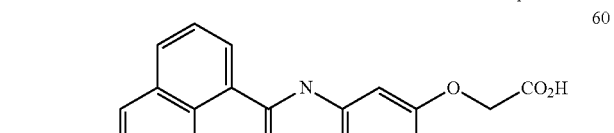

Compound 6

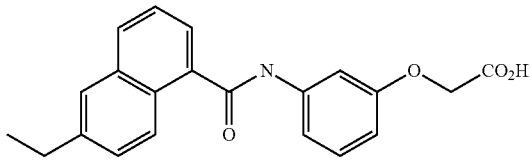

Compound 7

Compound 8

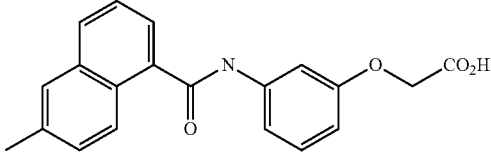

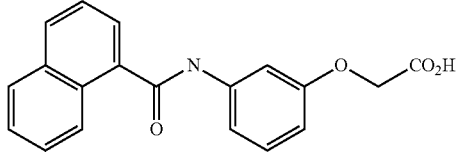

Compound 9

Compound 10

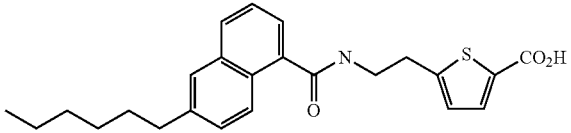

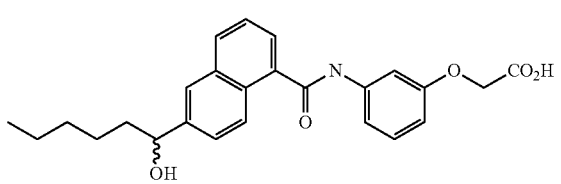

Compound 11

Compound 12

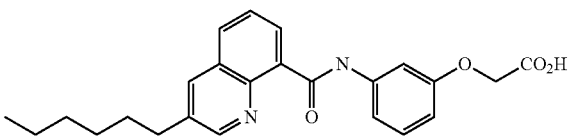

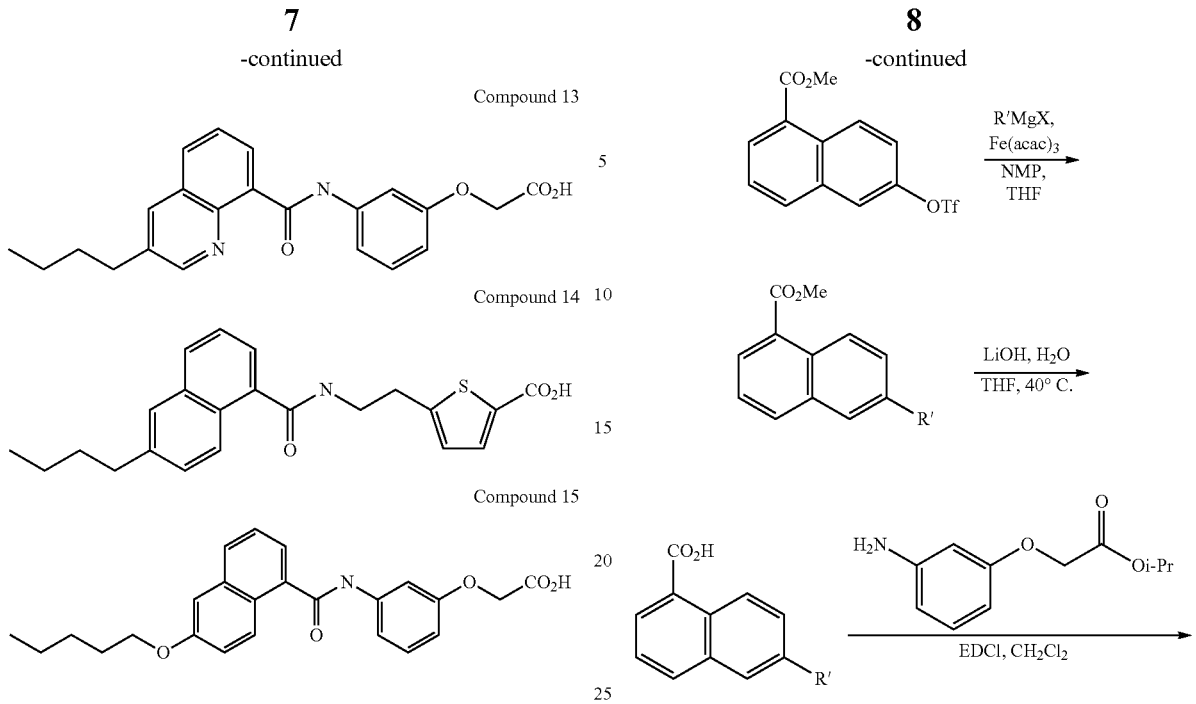
The compounds of the invention can be prepared in a variety of ways well known to those skilled in the art. Scheme 1 set forth below outlines an exemplary synthetic route to the compounds of the invention described in Examples 1-8.
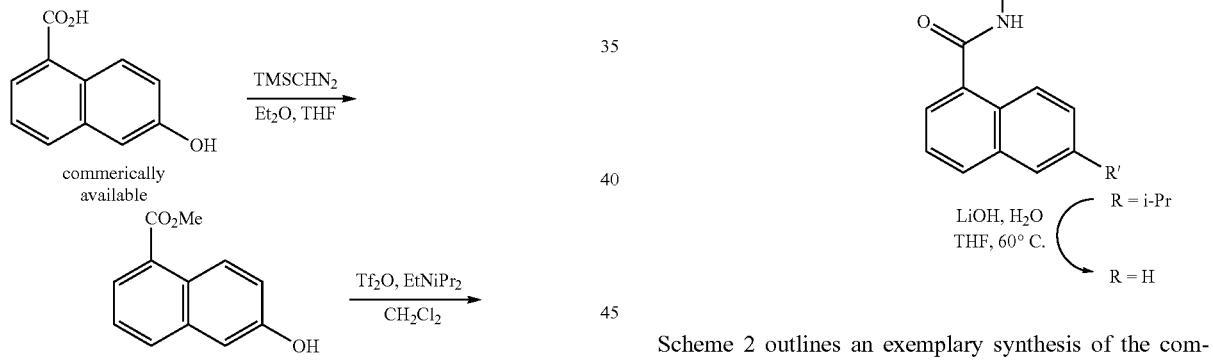
Scheme 2 outlines an exemplary synthesis of the compound of Example 9.
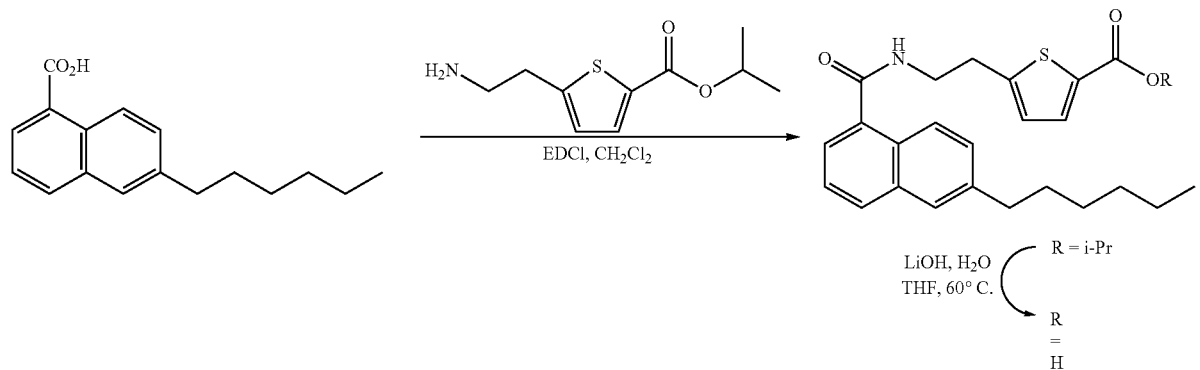

Scheme 3 sets forth an exemplary synthesis of the compounds of Examples 10 and 11.
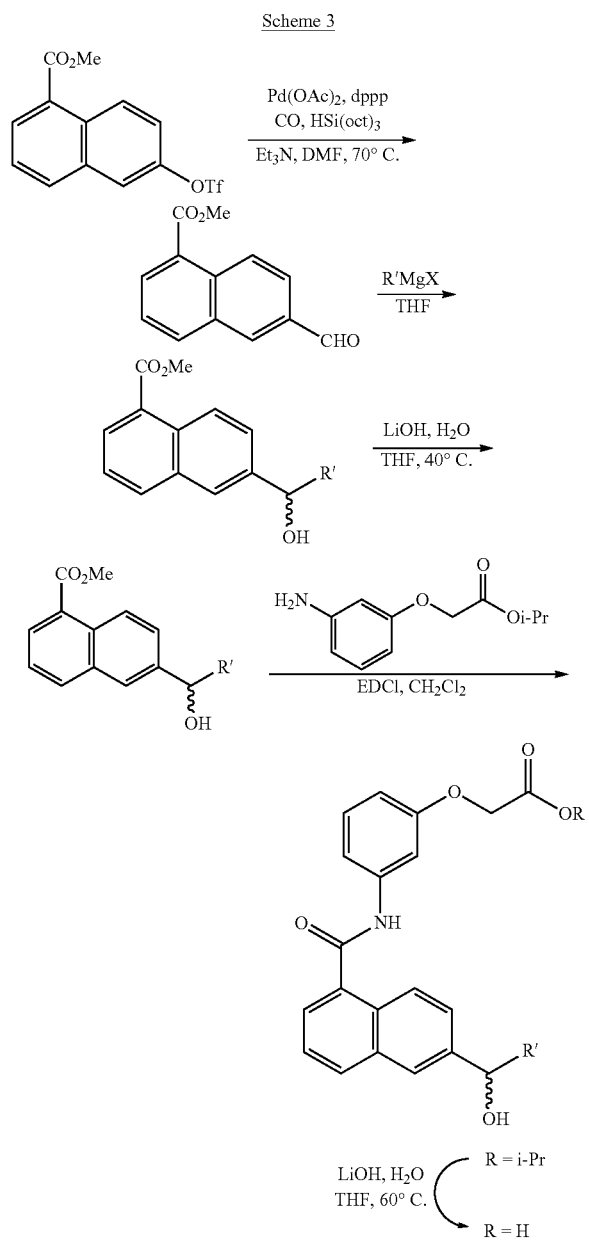
Scheme 4 sets forth an exemplary synthesis of the compounds of Examples 12 and 13.
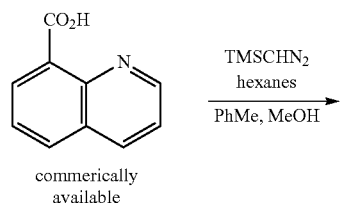
Scheme 5 sets forth an exemplary synthesis of the compound of Example 14.
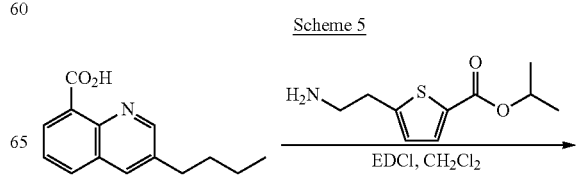

11
-continued
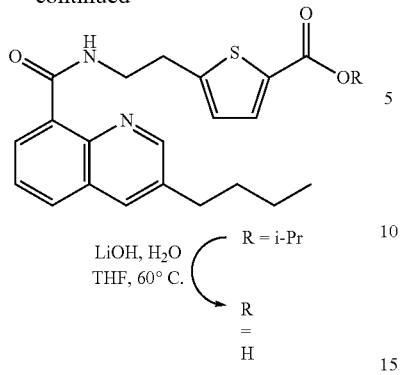
R = i-Pr
LiOH, H₂O
THF, 60° C.
R = H
Scheme 6 sets forth an exemplary synthesis of the compound of Example 15,
12
-continued
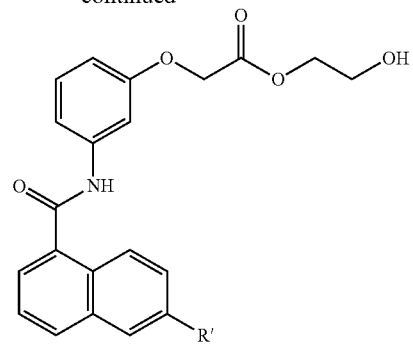
R' = n-butyl; 1-hydroxyhexyl
Scheme 6
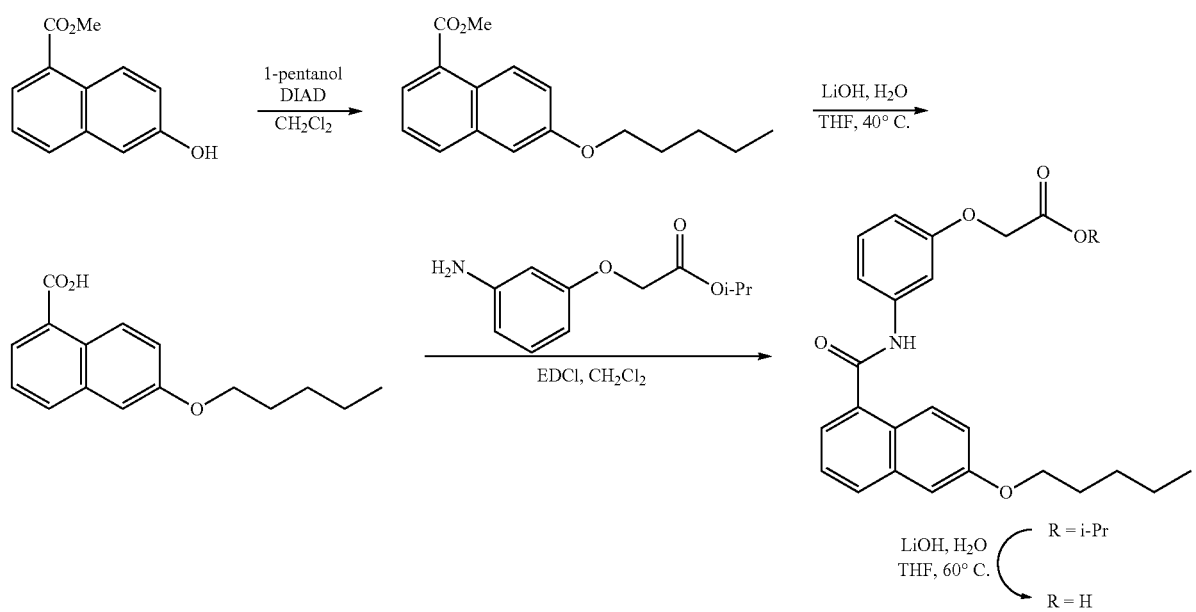
Scheme 7 sets forth an exemplary synthesis of the compounds of Examples 16 and 17.
Scheme 8 sets forth an exemplary synthesis of the compound of Example 18.
Scheme 7
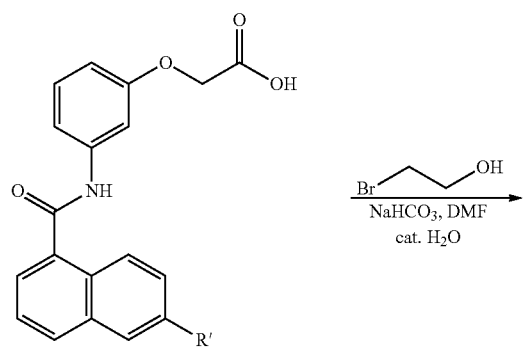
Scheme 8
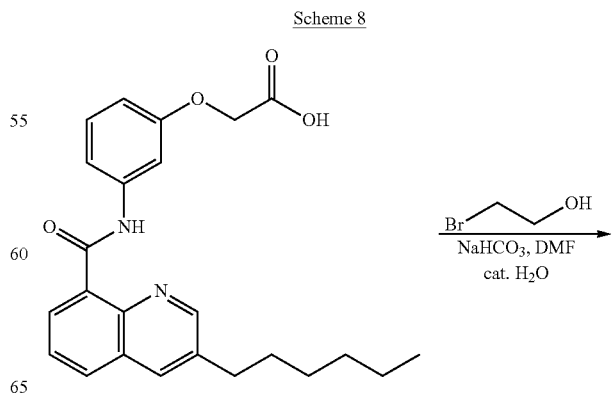

-continued
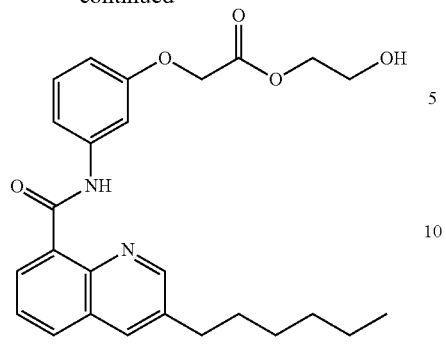
Data from running binding and activity studies on the compounds of the invention were carried out as described in the U.S. Pat. No. 7,427,685, the contents of which are incorporated herein by reference.

| Example # | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | hIP | hDP |
| 1 | ![structure] | 3 | 2 | 99 | NT | >10000 | NA | NA | NA | NA | NA | NA |
| 2 | ![structure] | 9 | 2 | 383 | NT | >10000 | NA | NA | NA | NA | NA | NA |
| 3 | ![structure] | 2 | 1 | 51 | NT | >10000 | NA | NA | NA | NA | NA | NA |
| 4 | ![structure] | 25 | 15 | 1205 | >10000 | 7682 | NA | NA | NA | NA | NA | NA |
| 5 | ![structure] | 10 | 5 | 30 | 7130 | 6917 | NA | NA | NA | NA | NA | NA |

-continued

| Example # | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | hIP | hDP |
| 6 | ethyl-naphthyl-C(O)NH-phenyl-O-CH2-CO2H | 21 | 5 | 112 | NT | >10000 | NA | NA | NA | NA | NA | NA |
| 7 | methyl-naphthyl-C(O)NH-phenyl-O-CH2-CO2H | 128 | 65 | 1188 | NT | >10000 | NA | NA | NA | NA | NA | NA |
| 8 | naphthyl-C(O)NH-phenyl-O-CH2-CO2H | 1424 | 83 | 4602 | NT | >10000 | NA | NA | NA | NA | NA | NA |
| 9 | hexyl-naphthyl-C(O)NH-CH2CH2-thienyl-CO2H | 75 | 25 | 3211 | 9401 | 2448 | NA | NA | NA | NA | NA | NA |
| 10 | (hydroxyhexyl)-naphthyl-C(O)NH-phenyl-O-CH2-CO2H | NT | 0.2 | 37 | NT | >10000 | NA | NA | NA | NA | NA | NA |

-continued

| Example # | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | hIP | hDP |
| 11 | [naphthalene amide with phenoxyacetic acid and hydroxypentyl substituent] | NT | 0.7 | 63 | NT | 5306 | NA | NA | NA | NA | NA | NA |
| 12 | [quinoline-8-carboxamide with phenoxyacetic acid and hexyl substituent] | 0.5 | 0.8 | 25 | 4681 | 2149 | NA | NA | 13266 | 6564 | NA | NA |
| 13 | [quinoline-8-carboxamide with phenoxyacetic acid and pentyl substituent] | NT | 2 | 27 | >10000 (cAMP) | 2059 | NA | NA | NA | NA | NA | NA |
| 14 | [quinoline-8-carboxamide with thiophene carboxylic acid and pentyl substituent] | NT | 12 | 350 | >10000 (cAMP) | 2033 | NA | NA | NA | NA | NA | NA |
| 15 | [naphthalene amide with phenoxyacetic acid and pentyloxy substituent] | NT | 25 | 201 | >10000 (cAMP) | 8480 | NA | NA | NA | NA | NA | NA |

The invention also relates to pharmaceutical compositions including at least one compound of structure I, the compound being alone or in combination with one or more pharmaceutically acceptable excipients. The invention also relates to methods for the treatment of glaucoma or ocular hypertension. Such methods can be performed, for example, by administering to a subject in need thereof an ophthalmically acceptable pharmaceutical composition containing a therapeutically effective amount of at least one compound of structure I.

An ophthalmically acceptable pharmaceutical composition is one that can be administered topically to the eye of a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the composition topically.

The pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition. Solutions for ophthalmic application are often prepared using physiological saline as a major vehicle. Other vehicles include polyvinyl alcohol, povidone, hydroxypropyl methyl cellulose, poloxamers, carboxymethyl cellulose, hydroxyethyl cellulose, and purified water. Examples of useful excipients also include preservatives, buffers, other pH adjustors, tonicity adjustors, surfactants, antioxidants, and chelating agents.

Useful preservatives include benzalkonium chloride, chlorobutanol, thimerosal, phenylmercuric acetate and phenylmercuric nitrate. Examples of buffers include phosphate, borate, sulfate, acetate, and citrate buffers. Acids or bases may be used to adjust the pH of the compositions as needed. Examples of tonicity agents include glycerin, mannitol, sodium chloride and potassium chloride. Useful surfactants include, for example, Tween 80. Examples of ophthalmically acceptable antioxidants include sodium metabisulfite, sodium thiosulfate, acetylcysteine, butylated hydroxyanisole and butylated hydroxytoluene. A useful chelating agent is edentate disodium.

Mixtures of two or more of any suitable excipients may be used. The aforementioned examples are not intended to limit the scope of the invention in any way.

The ingredients are usually used in the following amounts:

| Ingredient | Amount (Weight/Volume Percentage) |
| --- | --- |
| active ingredient | About 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

A therapeutically effective amount of at least one compound of structure I in the pharmaceutical composition disclosed herein is an amount useful to observe a therapeutic effect as compared to a placebo composition that, except for the absence of a compound of structure I, is otherwise identical to the pharmaceutical composition. The amount of at least one compound of structure I to administer depends on factors such as the intended therapeutic effects, the specific mammal in need thereof, the severity and nature of the mammal's condition, the manner of administration, the potency and pharmacodynamics of the particular compound, and the judgment of the prescribing physician. The therapeutically effective dosage of at least one compound of structure I is preferably in the range of about 0.5 or about 1 to about 100 mg/kg/day.

Also, an ophthalinically acceptable pharmaceutical composition should be packaged for single use, or contain a preservative to prevent contamination over multiple uses.

Aside from topical application to treat diseases affecting the eye including glaucoma, pharmaceutical compositions containing at least one compound of structure I can also be administered periocularly, intraocularly, or by other effective means available in the art.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, Reminton's Pharmaceutical Sciences, Mack Publishing Company, Easton, Pa., $16^{th}$ Edition, 1980).

Parenteral administration is generally characterized by subcutaneous, intramuscular, or intravenous injection. Injectables can be prepared as liquid solutions or suspensions, solid forms that can be reconstituted into solutions or suspensions prior to injection, or as emulsions. Suitable excipients include water, saline dextrose, glycerol, ethanol and the like. Such injectable pharmaceutical compositions may also contain minor amounts of non-toxic auxiliary substances such as wetting or emulsifying agents, pH buffers and the like. Examples mentioned herein are not intended to limit the scope of the invention in any way.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting, cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloroprostenol, fluprostenol, 13,14-dihydro-chloroprostenol, isopropyl unoprostone, latanoprost and the like.

Cannabinoids including CBI agonists such as WIN-55212-2 and CP-55940 and the like, or pharmaceutically acceptable salts or prodrugs thereof.

"Prodrug" refers to a compound which converts to a therapeutically active compound after administration and is used herein as it is generally understood in the art. Conversion of the prodrug into an activated form may occur by hydrolysis of an ester group or some other biologically labile group. Generally, but not necessarily, a prodrug is inactive or less active than the therapeutically active compound into which it is converted.

The following examples are intended only to illustrate the invention and should in no way be construed as limiting the invention.

EXAMPLES

Example 1

2-(3-(6-Hexyl-1-naphthamido)phenoxy)acetic acid

Step 1. Methyl 6-hydroxy-1-naphthoate

A solution of (trimethylsilyl)diazomethane (4.0 mL of a 2.0 M solution in $Et_2O$, 8.0 mmol) was added slowly to a solution of 6-hydroxy-1-naphthoic acid (commercially available from TCI, 1.50 g, 8.0 mmol) in THF (40 mL) at 0° C. After 1.5 h at 0° C., the reaction mixture was concentrated in vacuo and absorbed onto silica. The resulting residue was purified on 80 g silica gel (100% hexanes→100% EtOAc, gradient) to afford 910 mg (56%) of methyl 6-hydroxy-1-naphthoate.

Step 2. Methyl 6-(((trifluoromethyl)sulfonyl)oxy)-1-naphthoate

Diisopropylethylamine (2.35 mL, 13.5 mmol) and trifluoromethanesulfonic anhydride (0.95 mL, 5.6 mmol) were added sequentially to a solution of methyl 6-hydroxy-1-naphthoate (910 mg, 4.5 mmol) in $CH_2Cl_2$ (60 mL) at -78° C. After 1 h at -78° C., the reaction mixture was poured into saturated aqueous $NH_4Cl$ (30 mL). The resulting mixture was extracted with $CH_2Cl_2$ (3×50 mL). The combined organic phase was washed with brine (50 mL) then dried ($Na_2SO_4$), filtered and concentrated in vacuo. The resulting residue was purified on 80 g silica gel (100% hexanes→100% EtOAc, gradient) to afford 1.45 g (96%) of methyl 6-(((trifluoromethyl)sufonly)oxy)-1-naphthoate.

Step 3. Methyl 6-hexyl-1-naphthoate

In accordance with the procedure of Furstner (*Angew. Chem. Int. Ed.*, 2002, 41, 609-612), a solution of methyl 6-(((trifluoromethyl)sulfonyl)oxy)-1-naphthoate (334 mg, 1.0 mmol) and Fe(acac)$_3$ in THF (6 mL) and NMP (0.56 mL) was treated with n-hexylmagnesium bromide (1.2 mL of a 2.0 M solution in $Et_2O$, 2.4 mmol) at room temperature. After 30 min, the mixture was diluted with $Et_2O$ (20 mL) and quenched with 1 N aqueous HCl (5 mL). The phases were separated and the organic phase was washed with water (2×15 mL) and brine (15 mL), then dried ($Na_2SO_4$), filtered and concentrated in vacuo. The resulting residue was purified on 40 g silica gel (100% hexanes→20% EtOAc/hexanes, gradient) to afford 206 mg (76%) of methyl 6-hexyl-1-naphthoate.

Step 4. 6-Hexyl-1-naphthoic acid

Aqueous 1 N lithium hydroxide (3.6 mL, 3.6 mmol) was added to a solution of methyl 6-hexyl-1-naphthoate (198 mg, 0.73 mmol) THF (16 mL) in a scintillation vial. The vial was sealed and heated at 40° C. After 24 h, the reaction mixture was allowed to cool and the volatiles were evaporated under a stream of nitrogen. The residue was diluted with water (3 mL), acidified with 1 N aqueous HCl (5 mL) and extracted with EtOAc. (2×50 mL). The combined organic phase was dried ($Na_2SO_4$), filtered and concentrated in vacuo to afford 182 mg (97%) of 6-hexyl-1-naphthoic acid, which was used without hither purification.

Step 5. Isopropyl 2-(3-(6-hexyl-1-naphthamido)phenoxy)acetate

1-Ethyl-3-(3'-dimethylaminopropyl)-carbodiimide hydrochloride (EDCI, 157 mg) was added to a solution of 6-hexyl-1-naphthoic acid (161 mg, 0.63 mmol) and isopropyl 2-(3-aminophenoxy)acetate (131 mg, 0.63 mmol) in $CH_2Cl_2$ (6.3 mL) and the solution was stirred at room temperature overnight. The reaction was concentrated in vacuo, diluted with water (25 mL) and extracted with EtOAc (2×25 mL). The combined organic phase was washed with 1 N aqueous HCl (20 mL), saturated aqueous $NaHCO_3$ (20 mL) and brine (20 mL), then dried ($Na_2SO_4$), filtered and concentrated in vacuo. The crude residue was purified on 40 g silica (100% hexanes→100% EtOAc, gradient) to afford 65 mg (23%) of isopropyl 2-(3-(6-Hexyl-1-naphthamido)phenoxy)acetate.

Step 6.
2-(3-(6-Hexyl-1-naphthamido)phenoxy)acetic acid

Aqueous 1 N lithium hydroxide (0.5 mL, 0.5 mmol) was added to a solution of isopropyl 2-(3-(6-hexyl-1-naphthamido)phenoxy)acetate (44 mg, 0.98 mmol) in THF (0.5 mL) in a scintillation vial. The vial was sealed and heated at 60° C. After 40 h, the reaction mixture was allowed to cool and the volatiles were evaporated under a stream of nitrogen. The residue was diluted with water (2 mL), acidified with 1 N aqueous HCl (2 mL) and extracted with EtOAc (3×20 mL). The combined organic phase was washed with brine (10 mL), then dried ($Na_2SO_4$), filtered and concentrated in vacuo to afford 36 mg (90%) of the title compound.

Example 2

2-(3-(6-Pentyl-1-naphthamido)phenoxy)acetic acid

Step 1. Methyl 6-pentyl-1-naphthoate

In accordance with the procedure of Example 1, step 3, methyl 6-(((trifluoromethyl)sulfonyl)oxy)
1-naphthoate (334 mg, 1.0 mmol) n-pentylmagnesium bromide (1.2 mL of a 2.0 M solution in $Et_2O$, 2.4 mmol) were converted into 45 mg (18%) of methyl 6-pentyl-1-naphthoate.

Step 2. 6-Pentyl-1-naphthoic acid

In accordance with the procedure of Example 1, step 4, methyl 6-pentyl-1-naphthoate (45 mg, 0.18 mmol) was converted into 39 mg (91%) of 6-pentyl-1-naphthoic acid, which was used without further purification.

Step 3. Isopropyl
2-(3-(6-pentyl-1-naphthamido)phenoxy)acetate

In accordance with the procedure of Example 1, step 5, 6-pentyl-1-naphthoic acid (39 mg, 0.16 mmol) and isopropyl 2-(3-aminophenoxy)acetate (34 mg, 0.16 mmol) were converted into 17 mg (24%) of isopropyl 2-(3-(6-pentyl-1-naphthamido)phenoxy)acetate.

Step 4.
2-(3-(6-Pentyl-1-naphthamido)phenoxy)acetic acid

In accordance with the procedure of Example 1, step 6, isopropyl 2-(3-(6-pentyl-1-naphthamido)phenoxy)acetate (9 mg, 0.02 mmol) was converted into 7 mg (86%) of the title compound.

Example 3

2-(3-(6-Butyl-1-naphthamido)phenoxy)acetic acid

Step 1. Methyl 6-butyl-1-naphthoate

In accordance with the procedure of Example 1, step 3, methyl 6-(((trifluoromethyl)sulfonyl)oxy)-1-naphthoate (334 mg, 1.0 mmol) n-butylmagnesium chloride (1.2 mL, of a 2.0 M solution in THF, 2.4 mmol) were converted into 90 mg (37%) of methyl 6-butyl-1-naphthoate.

Step 2. 6-Butyl-1-naphthoic acid

In accordance with the procedure of Example 1, step 4, methyl 6-butyl-1-naphthoate (90 mg, 0.37 mmol) was converted into 50 mg (59%) of 6-butyl-1-naphthoic acid after purification on 12 g silica ($CH_2Cl_2$→15% $MeOH/CH_2Cl_2$, gradient).

Step 3. Isopropyl
2-(3-(6-butyl-1-naphthamido)phenoxy)acetate

In accordance with the procedure of Example 1, step 5, 6-butyl-1-naphthoic acid (50 mg, 0.22 mmol) and isopropyl 2-(3-aminophenoxy)acetate (46 mg, 0.22 mmol) were converted into 32 mg (35%) of isopropyl 2-(3-(6-butyl-1-naphthamido)phenoxy)acetate.

Step 4. 2-(3-(6-Butyl-1-naphthamido)phenoxy)acetic acid

In accordance with the procedure of Example 1, step 6, isopropyl 2-(3-(6-butyl-1-naphthamido)phenoxy)acetate (12 mg, 0.03 mmol) was converted into 9 mg (82%) of the title compound.

Example 4

2-(3-(6-Heptyl-1-naphthamido)phenoxy)acetic acid

Step 1. Methyl 6-heptyl-1-naphthoate

In accordance with the procedure of Example 1, step 3, methyl 6-(((trifluoromethyl)sulfonyl)oxy)-1-naphthoate (334 mg, 1.0 mmol) and n-heptylmagnesium bromide (2.4 mL of a 1.0 M solution in $Et_2O$, 2.4 mmol) were converted into 203 mg (71%) of methyl 6-heptyl-1-naphthoate.

Step 2. 6-Heptyl-1-naphthoic acid

In accordance with the procedure of Example 1, step 4, methyl 6-heptyl-1-naphthoate (203 mg, 0.71 mmol) was converted into 181 mg (94%) of 6-heptyl-1-naphthoic acid.

Step 3. Isopropyl
2-(3-(6-heptyl-1-naphthamido)phenoxy)acetate

In accordance with the procedure of Example 1, step 5, 6-heptyl-1-naphthoic acid (63 mg, 0.23 mmol) and isopropyl 2-(3-aminophenoxy)acetate (50 mg, 0.24 mmol) were converted into 32 mg (30%) of isopropyl 2-(3-(6-heptyl-1-naphthamido)phenoxy)acetate.

Step 4.
2-(3-(6-Heptyl-1-naphthamido)phenoxy)acetic acid

In accordance with the procedure of Example 1, step 6, isopropyl 2-(3-(6-heptyl-1-naphthamido)phenoxy)acetate (15 mg, 0.03 mmol) was converted into 10 mg (73%) of the title compound.

Example 5

2-(3-(6-Propyl-1-naphthamido)phenoxy)acetic acid

Step 1. Methyl 6-propyl-1-naphthoate

In accordance with the procedure of Example 1, step 3, methyl 6-(((trifluoromethyl)sulfonyl)oxy)-1-naphthoate (334 mg, 1.0 mmol) and n-propylmagnesium bromide (1.2 mL of a 2.0 M solution in Et$_2$O, 2.4 mmol) were converted into 169 mg (74%) of methyl 6-propyl-1-naphthoate.

Step 2. 6-Propyl-1-naphthoic acid

In accordance with the procedure of Example 1, step 4, methyl 6-propyl-1-naphthoate (169 mg, 0.74 mmol) was converted into 158 mg (quant.) of 6-propyl-1-naphthoic acid.

Step 3. Isopropyl 243-(d-propyl-1-naphthamido)phenoxy)acetate

In accordance with the procedure of Example 1, step 5, 6-propyl-1-naphthoic acid (50 mg, 0.23 mmol) and isopropyl 2-(3-aminophenoxy)acetate (50 mg, 0.24 mmol) were convened into 30 mg (32%) of isopropyl 2-(3-(6-propyl-1-naphthamido)phenoxy)acetate.

Step 4. 2-(3-(6-Propyl-1-naphthamido)phenoxy)acetic acid

In accordance with the procedure of Example 1, step 6, isopropyl 243-(6-propyl-1-naphthamido)phenoxy)acetate (15 mg, 0.03 mmol) was converted into 11 mg (82%) of the title compound.

Example 6

2-(3-(6-Ethyl-1-naphthamido)phenoxy)acetic acid

Step 1. Methyl 6-ethyl-1-naphthoate

In accordance with the procedure of Example 1, step 3, methyl 6-(((trifluoromethyl)sulfonyl)oxy)-1-naphthoate (334 mg, 1.0 mmol) and ethylmagnesium bromide (1.0 mL of a 3.0 M solution in Et$_2$O, 3.0 mmol) were convened into 145 mg (68%) of methyl 6-ethyl-1-naphthoate.

Step 2. 6-Ethyl-1-naphthoic acid

In accordance with the procedure of Example 1, step 4, methyl 6-ethyl-1-naphthoate (145 mg, 0.68 mmol) was converted into 112 mg (82%) of 6-ethyl-1-naphthoic acid.

Step 3. Isopropyl 2-(3-(6-ethyl-1-naphthamido)phenoxy)acetate

In accordance with the procedure of Example 1, step 5, 6-ethyl-1-naphthoic acid (51 mg, 0.25 mmol) and isopropyl 2-(3-aminophenoxy)acetate (64 mg, 0.31 mmol) were converted into 34 mg (34%) of isopropyl 243-(6-ethyl-1-naphthamido)phenoxy)acetate.

Step 4. 2-(3-(6-Ethyl-1-naphthamido)phenoxy)acetic acid

In accordance with the procedure of Example 1, step 6, isopropyl 2-(3-(6-ethyl-1-naphthamido)phenoxy)acetate (34 mg, 0.09 mmol) was converted into 19 mg (63%) of the title compound after purification by preparative thin layer chromatography eluting with 15% MeOH/CF$_2$Cl$_2$.

Example 7

2-(3-(6-Methyl-1-naphthamido)phenoxy)acetic acid

Step 1. Methyl 6-methyl-1-naphthoate

In accordance with the procedure of Example 1, step 3, methyl 6-(((trifluoromethyl)sulfonyl)oxy)-1-naphthoate (334 mg, 1.0 mmol) and methylmagnesium bromide (1.0 of a 3.0 M solution in Et$_2$O, 3.0 mmol) were converted into 185 mg (92%) of methyl 6-methyl-1-naphthoate.

Step 2. 6-Methyl-1-naphthoic acid

In accordance with the procedure of Example 1, step 4, methyl 6-methyl-1-naphthoate (185 mg, 0.92 mmol) was converted into 155 mg (90%) of 6-methyl-1-naphthoic acid.

Step 3. Isopropyl 2-(3-(6-methyl-1-naphthamido)phenoxy)acetate

In accordance with the procedure of Example 1, step 5, 6-methyl-1-naphthoic acid (65 mg, 0.35 mmol) and isopropyl 2-(3-aminophenoxy)acetate (86 mg, 0.41 mmol) were converted into 54 mg (41%) of isopropyl 2-(3-(6-methyl-1-naphthamido)phenoxy)acetate.

Step 4. 2-(3-(6-Methyl-4-naphthamido)phenoxy)acetic acid

In accordance with the procedure of Example 1, step 6, isopropyl 2-(3-(6-methyl-1-naphthamido)phenoxy)acetate (54 mg, 0.14 mmol) was converted into 35 mg (73%) of the title compound after purification by preparative thin layer chromatography eluting with 15% MeOH/CH$_2$Cl$_1$.

Example 8

2-(3-(1-Naphthamido)phenoxy)acetic acid

Step 3. Isopropyl 2-(3-(1-naphthamido)phenoxy)acetate

In accordance with the procedure of Example 1, step 5, 1-naphthoic acid (40 mg, 0.23 mmol) and isopropyl 2-(3-aminophenoxy)acetate (50 mg, 0.24 mmol) were converted into 30 mg (36%) of isopropyl 2-(3-(1-naphthamido)phenoxy)acetate.

Step 4. 2-(3-(1-Naphthamido)phenoxy)acetic acid

In accordance with the procedure of Example 1, step 6, isopropyl 2-(3-(1-naphthamido)phenoxy)acetate (14 mg, 0.04 mmol) was converted into 12 mg (97%) of the title compound.

Example 9

5-(2-(6-Hexyl-1-naphthamido)ethylthiophene-2-carboxylic acid

Step 1. Isopropyl 5-(2-(6-hexyl-1-naphthamido)ethyl)thiophene-2-carboxylate

In accordance with the procedure of Example 1, step 5, 6-hexyl-1-naphthoic acid (52 mg, 0.20 mmol) and isopropyl 5-(2-aminoethyl)thiophene-2-carboxylate (see U.S. Provisional Patent Application Ser. No. 61/298,428, the entire contents of which are incorporated herein by reference, 43 mg, 0.20 mmol) were converted into 74 mg (81%) of isopropyl 5-(2-(6-hexyl-1-naphthamido)ethyl)thiophene-2-carboxylate.

Step 2. 5-(2-(6-Hexyl-1-naphthamido)ethyl)thiophene-2-carboxylic acid

In accordance with the procedure of Example 1, step 6, isopropyl 5-(2-(6-hexyl-1-naphthamido)ethyl)thiophene-2- carboxylate (14 mg, 0.03 mmol) was converted into 6.5 mg (51%) of the title compound after purification on 12 g silica ($CH_2Cl_2 \rightarrow 20\%$ $MeOH/CH_2Cl_2$, gradient).

Example 10

2-(3-(6-(1-hydroxyhexyl)-1-naphthamido)phenoxy) acetic acid

Step 1. Methyl 6-formyl-1-naphthoate

Carbon monoxide (CO) gas was slowly bubbled through a solution of methyl 6-(((trifluoromethyl)sulfonyl)oxy)-1-naphthoate (334 mg, 1.0 mmol), $Pd(OAc)_2$ (22 mg, 0.10 mmol), 1,3-bis-(diphenylphosphino)propane (40 mg, 0.10 mmol) and triethylamine (0.28 mL, 2.0 mmol) an DMF (8.3 mL). After 15 min, trioctylsilane (0.90 mL, 2.0 mmol) was added as bubbling continued. The mixture was heated at 70° C., continuing to bubble CO into the solution. After 6 h at 70° the bubbling CO was replaced with a balloon of CO and the reaction mixture was stirred overnight. After 18 h at 70° C., the reaction was cooled to room temperature, diluted with EtOAc (150 mL) and washed with water (3×50 mL) and brine (50 mL). The organic phase was dried ($Na_2SO_4$), filtered and concentrated in vacuo. The resulting residue was purified on 40 g silica gel (100% hexanes→25% EtOAc/hexanes, gradient) to afford 78 mg (36%) of methyl 6-formyl-1-naphthoate.

Step 2. Methyl 6-(1-hydroxyhexyl)-1-naphthoate

A solution of methyl 6-formyl-1-naphthoate (36 mg, 0.17 mmol) in THE (1.7 mL) was cooled to 0° C. and treated with n-pentylmagnesium bromide (0.1 mL of a 2.0 M solution in $Et_2O$, 0.2 mmol). The cooling bath was removed and after stirring at room temperature for 1 h the reaction was quenched with 1 N aqueous HCl, diluted with water (10 mL) and extracted with EtOAc (3×10 The combined organic phase was dried ($Na_2SO_4$), filtered and concentrated in vacuo. The resulting residue was purified on 12 g silica gel (100% hexanes→40% EtOAc/hexanes, gradient) to afford 34 mg (71%) of methyl 6-(1-hydroxyhexyl)-1-naphthoate.

Step 3. 6-(1-Hydroxyhexyl)-1-naphthoic acid

In accordance with the procedure of Example 1, step 4, methyl 6-(1-hydroxyhexyl)-1-naphthoate (34 mg, 012 mmol) was converted into 29 mg (89%) of 6-(1-hydroxyhexyl)-1-naphthoic acid.

Step 4. Isopropyl 2-(3-(6-(1-hydroxyhexyl)-1-naphthamido)phenoxy)acetate

In accordance with the procedure of Example 1, step 5, 6-(1-hydroxyhexyl)-1-naphthoic acid (29 mg, 0.11 mmol) and isopropyl 2-(3-aminophenoxy)acetate (23 mg, 0.11 mmol) were converted into 16 mg (33%) of isopropyl 2-(3-(6-(1-hydroxyhexyl)-1-naphthamido)phenoxy)acetate.

Step 5. 2-(3-(6-(1-Hydroxyhexyl)-1-naphthamido) phenoxy)acetic acid

In accordance with the procedure of Example 1, step 6, isopropyl 2-(3-(6-(1-hydroxyhexyl)-1-naphthamido)phenoxy)acetate (9 mg, 0.14 mmol) was converted into 8 mg (quant.) of the title compound.

Example 11

2-(3-(6-(1-Hydroxybutyl)-1-naphthamido)phenoxy) acetic acid

Step 1. Methyl 6-(1-hydroxybutyl)-1-naphthoate

In accordance with the procedure of Example 10, step 2, methyl 6-formyl-1-naphthoate (35 mg, 0.16 mmol) and n-propylmagnesium chloride (0.1 mL of a 2.0 M solution in $Et_2O$, 0.2 mmol) were converted into 14 mg (33%) of methyl 6-(1-hydroxybutyl)-1-naphthoate.

Step 2. 6-(1-Hydroxybutyl)-1-naphthoic acid

In accordance with the procedure of Example 1, step 4, methyl 6-(1-hydroxybutyl)-1-naphthoate (14 mg, 0.05 mmol) was converted into 13 mg (98%) of 641-hydroxybutyl)-1-naphthoic acid.

Step 3. Isopropyl 2-(3-(6-(1-hydroxybutyl)-1-naphthamido)phenoxy)acetate

In accordance with the procedure of Example 1, step 5, 6-(1-hydroxybutyl)-1-naphthoic acid (13 mg, 0.05 mmol) and isopropyl 2-(3-aminophenoxy)acetate (11 mg, 0.05 mmol) were converted into 11 mg (47%) of isopropyl 2-(3-(6-(1-hydroxybutyl)-1-naphthamido)phenoxy)acetate.

Step 5. 2-(3-(6-(1-Hydroxybutyl)-1-naphthamido) phenoxy)acetic acid

In accordance with the procedure of Example 1, step 6, isopropyl 2-(3-(6-(1-hydroxybutyl)-1-naphthamido)phenoxy)acetate (5 mg, 0.01 mmol) was converted into 4 mg (89%) of the title compound.

Example 12

2-(3-(3-Hexylquinoline-8-carboxamido)phenoxy) acetic acid

Step 1. Methyl quinoline-8-carboxylate

A solution of (trimethylsilyl)diazomethane (8.0 mL of a 2.0 M solution in hexanes, 16.0 mmol) was added slowly to a suspension of quinoline-8-carboxylic acid (2.0 g, 11.5 mmol) in toluene (80 mL) and MeOH (12 mL) at 0° C. After 30 min at 0° C., the reaction mixture was warmed to room temperature and stirred for 64 h. Aqueous acetic acid was added and then enough saturated aqueous $Na_2CO_3$ was added to bring the pH to 7.5. The layers were separated and the aqueous phase was extracted with EtOAc. The combined organic phase was dried ($MgSO_4SO_4$), filtered and concentrated in vacuo. The resulting brown oil was purified on 40 g silica gel (2:1 $CH_2Cl_2$/EtOAc) to afford 1.72 g (80%) of methyl quinoline-8-carboxylate.

Step 2. Methyl 3-hydroxyquinoline-8-carboxylate

30% Hydrogen peroxide (1.55 mL) was added to a solution of methyl quinoline 8-carboxylate (1.43 g, 7.64 mmol) in acetic acid (10.9 mL, 190 mmol). The mixture was heated at 70° C. for 3 h. The solution was cooled in an ice bath and a solution of $NaHCO_3$ (16 g, 190 mmol) in water (130 mL) was added. The mixture was warmed to room temperature and chloroform was added. A solid, inseparable in both layers, was removed by filtration to give 546 mg of methyl 3-hydroxyquinoline-8-carboxylase. The filtrate was separated and the aqueous layer was extracted with chloroform (3×). The combined organic layers were dried (MgSO$_4$), filtered and concentrated in vacuo. Trituration with CH$_2$Cl$_2$ afforded 113 mg more product for a total yield of 659 mg (42%) of methyl 3-hydroxyquinoline-8-carboxylate Step 3. Methyl 3-(((trifluoromethyl)sulfonyl)oxy) quinoline-8-carboxylate Trifluoromethanesulfonic anhydride (0.55 mL, 3.4 mmol) was added to a solution of methyl 3-hydroxyquinoline-8-carboxylate (650 mg, 3.2 mmol) in pyridine (2.3 mL) and CH$_2$Cl$_2$ (13 mL) at 0° C. The reaction mixture was allowed to warm to room temperature. After 3 h, additional trifluoromethanesulfonic anhydride (0.55 mL, 3.4 mmol) was added and the reaction was stirred for an additional 18 h. Saturated aqueous NaHCO$_3$ (20 mL) was added and the layers were separated. The aqueous phase was extracted with CH$_2$Cl$_2$ (3×). The combined organic phase was dried (MgSO$_4$), filtered and concentrated in vacuo. The resulting residue was purified on silica gel eluting with CH$_2$Cl$_2$ to afford 971 mg (91%) of methyl 3-((((trifluoromethyl)sulfonyl)oxy)quinoline-8-carboxylate.

Step 4. Methyl 3-hexylquinoline-8-carboxylate

Methyl 3-(((trifluoromethyl)sulfonyl)oxy)quinoline-8-carboxylate (538 mg, 1.6 mmol), hexylboronic acid (415 mg, 3.2 mmol) and Cs$_2$CO$_3$ (779 mg, 2.4 mmol) were suspended in toluene (30 mL). The mixture was purged with nitrogen then tetrakis(triphenylphosphine)palladium (0) (55 mg, 0.05 mmol) was added. The reaction was sealed and heated at 95° C. for 16 h. The mixture was cooled and filtered through celite, rinsing with excess CH$_2$Cl$_2$. The filtrate was concentrated in vacuo. The resulting oil was purified on 40 g silica gel (19:1 CH$_2$Cl$_2$/methyl t-butyl ether) to afford 178 mg (41%) of methyl 3-hexylquinoline-8-carboxylate.

Step 5, 3-Hexylquinoline-8-carboxylic acid

In accordance with the procedure of Example 1, step 4, methyl 3-hexylquinoline-8-carboxylate (332 mg, 1.2 mmol) was converted at room temperature into 299 mg (95%) of 3-hexylquinoline-8-carboxylic acid, which was used without further purification.

Step 6. Isopropyl 2-(3-(3-hexylquinoline-8-carboxamido)phenoxy)acetate

To a solution of 3-hexylquinoline-8-carboxylic acid (170 mg, 0.66 mmol), isopropyl 2-(3-aminophenoxy)acetate (207 mg, 0.99 mmol) and N-methylmorpholine (0.18 mL, 1.65 mmol) in DMF (2.0 mL) was added O-(7-azabenzotriazol-1-yl)-N,N,N',N'-tetramethyluronium hexafluorophosphate (HATU) (380 mg, 1.0 mmol) and the solution was stirred at room temperature for 16 h. The DMF was removed in vacuo and the residue was partitioned between EtOAc and water. The organic phase was washed with saturated aqueous NaHCO$_3$ (2×) then dried (MgSO$_4$), filtered and concentrated in vacuo. The resulting residue was purified on 12 g silica gel eluting (17:3 hexanes/EtOAc) to afford 259 mg (87%) of isopropyl 2-(3-(3-hexylquinoline-8-carboxamido)phenoxy) acetate.

Step 7. 2-(3-(3-Hexylquinoline-8-carboxamido)phenoxy)acetic acid

Aqueous 2 N lithium hydroxide (0.7 mL, 1.4 mmol) and water (0.7 mL) were added to a solution of isopropyl 2-(3-(3-hexylquinoline-8-carboxamido)phenoxy)acetate (210 mg, 0.47 mmol) in THF (5.0 mL) and the solution was stirred at room temperature. After 20 h, the THF was removed in vacuo. The residual aqueous phase was adjusted to pH 4-5 with 1 N aqueous HCl and extracted with EtOAc (3×). The combined organic phase was dried (MgSO$_4$), filtered and concentrated in vacuo to afford 177 mg (93%) of the title compound.

Example 13

2-(3-(3-Butylquinoline-8-carboxamido)phenoxy) acetic acid

Step 1. Methyl 3-butylquinoline-8-carboxylate

In accordance with the procedure of Example 12, step 4, methyl 3-(((trifluoromethyl)sulfonyl)oxy)quinoline-8-carboxylate (269 mg, 0.8 mmol) and butylboronic acid (162 mg, 1.6 mmol) were converted into 112 mg (57%) of methyl 3-butylquinoline-8-carboxylate after purification on 40 g silica gel (100% hexanes 50% EtOAc/hexanes, gradient).

Step 2. 3-Butylquinoline-8-carboxylic acid

In accordance with the procedure of Example 1, step 4, methyl 3-butylquinoline-8-carboxylate (112 mg, 0.46 mmol) was converted into 104 mg (99%) of 3-butylquinoline-8-carboxylic acid, which was used without further purification.

Step 6. Isopropyl 2-(3-(3-butylquinoline-8-carboxamido)phenoxy)acetate

In accordance with the procedure of Example 1, step 5, 3-butylquinoline-8-carboxylic acid (52 mg, 0.23 mmol) and isopropyl 2-(3-aminophenoxy)acetate (47 mg, 0.23 mmol) were converted into 29 mg (30%) of isopropyl 2-(3-(3-butylquinoline-8-carboxamido)phenoxy)acetate.

Step 7. 2-(3-(3-Butylquinoline-8-carboxamido)phenoxy)acetic acid

In accordance with the procedure of Example 1 step 6, isopropyl 2-(3-(3-butylquinoline-8-carboxamido)phenoxy) acetate (5 mg, 0.012 mmol) was converted into 3.7 mg (82%) of the title compound.

Example 14

5-(2-(3-Butylquinoline-8-carboxamido)ethyl) thiophene-2-carboxylic acid

Step 1. Isopropyl 5-(2-(3-butylquinoline-8-carboxamido)ethyl)thiophene-2-carboxylate In accordance with the procedure of Example 1, step 5, 3-butylquinoline-8-carboxylic acid (26 mg, 0.11 mmol) and isopropyl 5-(2-aminoethyl)thiophene-2-carboxylate (24 mg, 0.11 mmol) were converted into 33 mg (69%) of isopropyl 5-(2-(3-butylquinoline-8-carboxamido)ethyl)thiophene-2-carboxylate.

Step 2. 5-(2-(3-Butylquinoline-8-carboxamido)ethyl)
thiophene-2-carboxylic acid

In accordance with the procedure of Example 1, step 6, isopropyl 5-(2-(3-butylquinoline-8-carboxamido)ethyl) thiophene-2-carboxylate (15 mg, 0.035 mmol) was converted into 13 mg (96%) of the title compound.

Example 15

2-(3-(6-(Pentyloxy)-1-naphthamido)phenoxy)acetic acid

Step 1. Methyl 6-(pentyloxy)-1-naphthoate

Triphenylphosphine (197 mg, 0.75 mmol) and diisopropyl azodicarboxylate (116 □L, 0.60 mmol) were added sequentially to a solution of methyl 6-hydroxy-1-naphthoate (101 mg, 0.50 mmol) and 1-pentanol (44 mg, 0.50 mmol) in $CH_2Cl_2$ (2.5 mL) at room temperature. After 38 h, the reaction mixture was concentrated in vacuo. The residue was suspended in EtOAc (20 mL) and washed with water (3×10 mL) and brine (10 mL). The organic phase was dried ($Na_2SO_4$), filtered and concentrated in vacuo. The resulting residue was purified on 12 g silica gel (100% hexanes 50% EtOAc/hexanes, gradient) to afford 135 mg (99%) of methyl 6-(pentyloxy)-1-naphthoate.

Step 2. 6-(Pentyloxy)-1-naphthoic acid

In accordance with the procedure of Example 1, step 4, methyl 6-(pentyloxy)-1-naphthoate (135 mg, 0.50 mmol) was converted into 129 mg (quant.) of 6-(pentyloxy)-1-naphthoic acid, which was used without further purification.

Step 3. Isopropyl 2-(3-(6-(pentyloxy)-1-naphthamido)phenoxy)acetate

In accordance with the procedure of Example 1, step 5, 6-(pentyloxy)-1-naphthoic acid (129 mg, 0.50 mmol) and isopropyl 2-(3-aminophenoxy)acetate (105 mg, 0.50 mmol) were converted into 50 mg (22%) of isopropyl 2-(3-(6-(pentyloxy)-1-naphthamido)phenoxy)acetate.

Step 4, 2-(3-(6-(Pentyloxy)-1-naphthamido)phenoxy)acetic acid

In accordance with the procedure of Example 1, step 6, isopropyl 2-(3-(6-(pentyloxy)-1-naphthamido)phenoxy)acetate (5.7 mg, 0.013 mmol) was converted into 5 mg (97%) of the title compound.

Example 16

2-Hydroxyethyl 2-(3-(6-butyl-1-naphthamido)phenoxy)acetate

2-Bromoethanol was added to a 1 dram vial containing a mixture of 2-(3-(6-butyl-1-naphthamido)phenoxy)acetic acid (27 mg, 0.07 mmol), $NaHCO_3$ (6 mg, 0.07 mmol) and DMF (03 mL). A single drop of water from a 22 gauge needle was added and the vial was sealed under nitrogen and heated at 70° C. After several days, the mixture was cooled to room temperature and diluted with EtOAc (20 The organic mixture was and washed with water (2×5 mL) and brine (5 mL) then dried ($Na_2SO_4$), filtered and concentrated in vacuo. The resulting residue was purified on 4 g silica gel (100% hexanes→100% EtOAc, gradient) to afford 24 mg (69%) of the title compound.

Example 17

2-Hydroxyethyl 2-(3-(6-(1-hydroxyhexyl)-1-naphthamido)phenoxy)acetate

In accordance with the procedure of Example 16, 2-(3-(6-(1-hydroxyhexyl)-1-naphthamido)phenoxy)acetic acid (8 mg, 0.019 mmol) was converted to 6 mg (66%) of the title compound.

Example 18

2-Hydroxyethyl 2-(3-(3-hexylquinoline-8-carboxamido)phenoxy)acetate

In accordance with the procedure of Example 16, 2-(3-(3-hexylquinoline-8-carboxamido)phenoxy)acetic acid (30 mg, 0.074 mmol) was converted to 14 mg (42%) of the title compound.

In Vivo Data

Isopropyl 2-(3-(6-hexyl-1-naphthamido)phenoxy)acetate was tested in normotensive dogs at 0.05%, dosing once daily for 5 days. The maximum intraocular pressure (IOP) decrease from baseline was 4.7 mmHg (28%) at 30 h; the maximum ocular surface hyperemia (OSH) score was 1.0 at 26 h. This compound was also tested in laser induced hypertensive monkeys, using one single day dose. At 0.05%, the maximum IOP decrease from baseline was 17.1 mmHg (48%) at 24 h.

Isopropyl 2-(3-(6-(1-hydroxyhexyl)-1-naphthamido)phenoxy)acetate was tested in normotensive dogs at two concentrations, dosing once daily for 5 days. At 0.005%, the maximum intraocular pressure (IOP) decrease from baseline was 4.1 mmHg (22%) at 4 h; the maximum ocular surface hyperemia (OSH) score was 1.6 at 2 h. At 0.01%, the maximum intraocular pressure (IOP) decrease from baseline was 4.4 mmHg (26%) at 4 h; the maximum ocular surface hyperemia (OSH) score was 1.5 at 50 h. This compound was also tested in laser-induced hypertensive monkeys at two concentrations, using one single day dose. At 0.005%, the maximum IOP decrease from baseline was 8.1 mmHg (30%) at 24 h. At 0.01%, the maximum IOP decrease from baseline was 15.4 mmHg (42%) at 24 h.

Isopropyl 2-(3-(6-butyl-1-naphthamido)phenoxy)acetate was tested in normotensive dogs at 0.01%, dosing once daily for 4 days. The maximum intraocular pressure (IOP) decrease from baseline was 5.1 mmHg (26%) at 78 h; the maximum ocular surface hyperemia (OSH) score was 0.9 at 4 h. This compound was also tested in laser-induced hypertensive monkeys, using one single day dose. At 0.01%, the maximum IOP decrease from baseline was 14.1 mmHg (38%) at 24 h.

Isopropyl 2-(3-(3-hexylquinoline-8-carboxamido)phenoxy)acetate was tested in normotensive dogs at 0.01%, dosing once daily for 5 days. The maximum intraocular pressure (IOP) decrease from baseline was 2.8 mmHg (14%) at 100 h; the maximum ocular surface hyperemia (OSH) score was 0.8 at 28 h. This compound was also tested in laser induced hypertensive monkeys, using one single day dose. At 0.01%, the maximum IOP decrease from baseline was 8.8 mmHg (19%) at 6 h.

While this invention has been described with respect to these specific examples, it is understood that other modifications and variations are possible without departing from the spirit of the invention.

What is claimed is:

1. A compound of the structure:

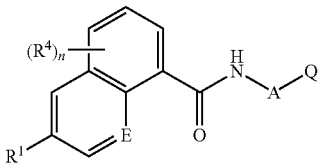

wherein:
- E is C or N;
- A is —(CH$_2$)$_m$—Ar—(CH$_2$)$_o$— wherein Ar is phenylene or thiophenylene, the sum of m and o is from 1 to 4, and wherein one CH$_2$ may be substituted with S or O;
- Q is —CO$_2$R$^2$, —CH$_2$OR$^2$, —CONR$^2$R$^3$, —COR$^3$, —SO$_2$R$^3$ or tetrazol-5-yl;
- R$^1$ is H, alkoxy, or C$_1$-C$_{20}$ linear alkyl, branched alkyl, or cycloalkyl, optionally substituted with one or more —OH moieties;
- R$^2$ is hydrogen, C$_1$-C$_6$ alkyl, hydroxyethyl, CF$_3$, phenyl, or biphenyl;
- R$^3$ is hydrogen, C$_1$-C$_6$ linear or branched alkyl, —COR$^2$ or —SO$_2$R$^2$;
- each R$^4$ is independently selected from F, Cl, I, or Br; and
- n is 0 to 6;

or a pharmaceutically acceptable salt thereof.

2. The compound of claim 1 wherein R$^1$ is C$_1$-C$_{10}$ alkyl.
3. The compound of claim 1 wherein R$^1$ is C$_6$ alkyl.
4. The compound of claim 1 wherein R$^2$ is hydroxyethyl.
5. The compound of claim 1 having any one of the following structures:

Compound 1

Compound 2

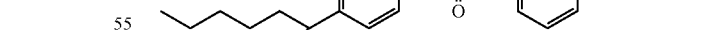

Compound 3

Compound 4

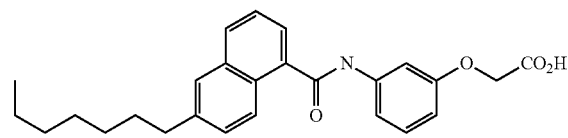

Compound 5

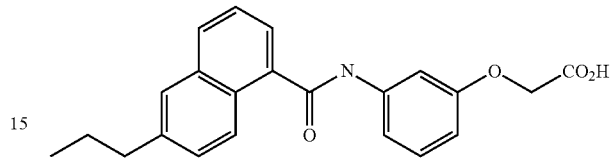

Compound 6

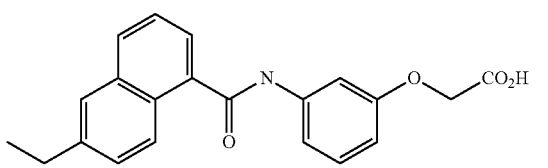 [SMILES: CCc1ccc2c(C(=O)Nc3cccc(OCC(=O)O)c3)cccc2c1]

Compound 7

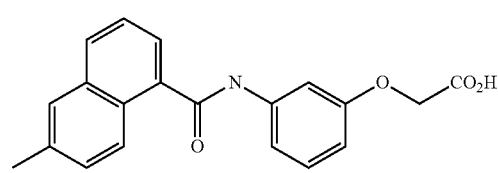 [SMILES: Cc1ccc2c(C(=O)Nc3cccc(OCC(=O)O)c3)cccc2c1]

Compound 8

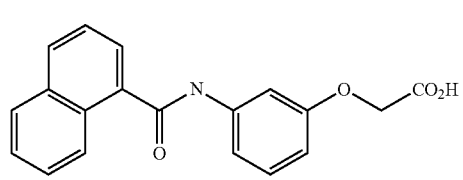 [SMILES: O=C(O)COc1cccc(NC(=O)c2cccc3ccccc23)c1]

Compound 9

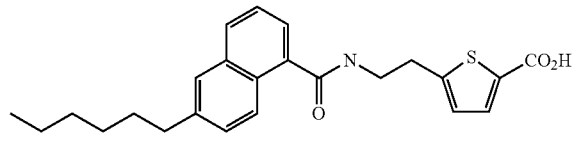

Compound 10

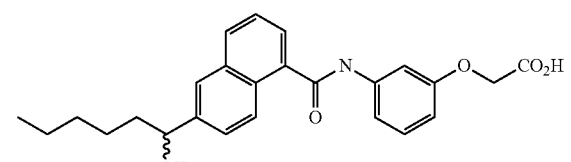

Compound 11

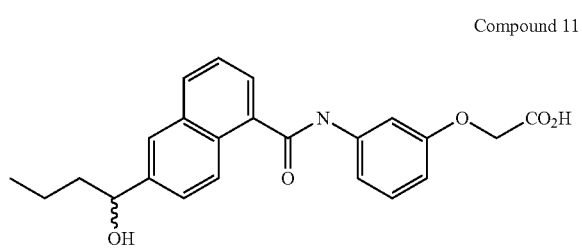

Compound 12

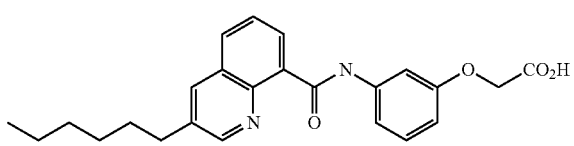

Compound 13

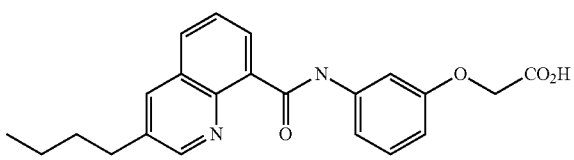 [SMILES: CCCCc1cnc2c(C(=O)Nc3cccc(OCC(=O)O)c3)cccc2c1]

Compound 14

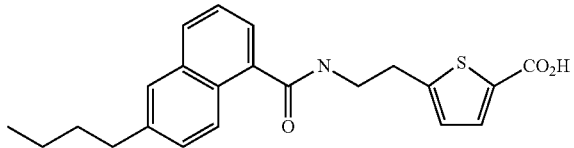 [SMILES: CCCCc1cnc2c(C(=O)NCCc3ccc(C(=O)O)s3)cccc2c1]

Compound 15

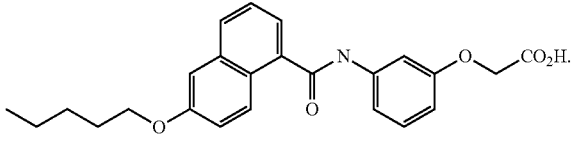

6. A pharmaceutical composition comprising at least one compound of claim 1, the compound being present alone or in combination with one or more pharmaceutically acceptable excipients.

7. A composition comprising at least one compound according to claim 1, wherein the composition is a liquid which is ophthalmically acceptable.

8. A method for the treatment of glaucoma or ocular hypertension comprising administering to a subject in need thereof a therapeutically effective amount of at least one compound to claim 1.

9. The method of claim 8 wherein the subject is human.

10. A method of reducing intraocular pressure comprising administering to a subject in need thereof a therapeutically effective amount of at least one compound of claim 1.

11. The method of claim 10 wherein the subject is human.

* * * * *